US00PP34167P2

(12) United States Plant Patent
Robacker et al.

(10) Patent No.: US PP34,167 P2
(45) Date of Patent: Apr. 26, 2022

(54) ***ABELIA* PLANT NAMED '00-BC-47-7R'**

(50) Latin Name: ***Abelia* hybrid**
Varietal Denomination: 00-BC-47-7R

(71) Applicant: University of Georgia Research Foundation, Inc., Athens, GA (US)

(72) Inventors: Carol Robacker, Peachtree City, GA (US); Allen Byous, Thomaston, GA (US); Sherrod Baden, Milner, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/317,291

(22) Filed: May 11, 2021

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02
See application file for complete search history.

(56) References Cited

PUBLICATIONS https://www.starrosesandplants.com/plants/abelia-apple-perfection/; Jul. 29, 2021; 2 pages.*
https://www.bestliners.com/wp-content/uploads/2020/12/catf20s21.pdf; Dec. 2020; 2 pages.*
https://en.wikipedia.org/wiki/Spring_(season); Jul. 29, 2021; 1 page.*

* cited by examiner

*Primary Examiner* — Kent L Bell
(74) *Attorney, Agent, or Firm* — Thomas Horstemeyer, LLP

(57) ABSTRACT

A new and distinctive cultivar of *Abelia* plant named '00-BC-47-7R' characterized by a combination of uniform, compact, mounding growth habit; glossy dark green foliage in the summer; relatively short height; white flowers and greyed-orange or yellow-green sepals; and heavy blooming from May to September.

6 Drawing Sheets

Figure 2A:
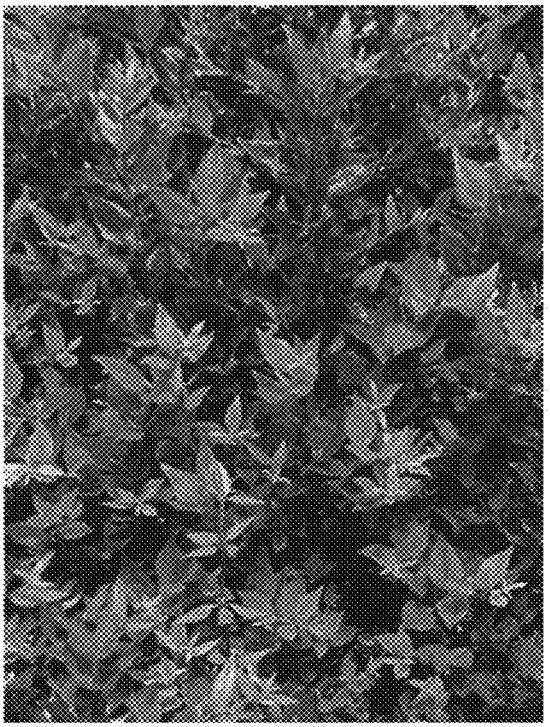
Figure 2B:
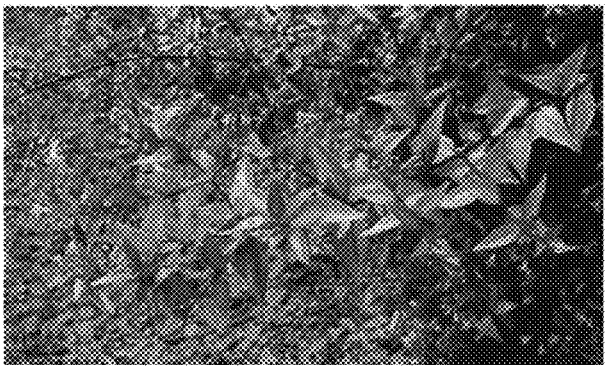
Figure 2C:
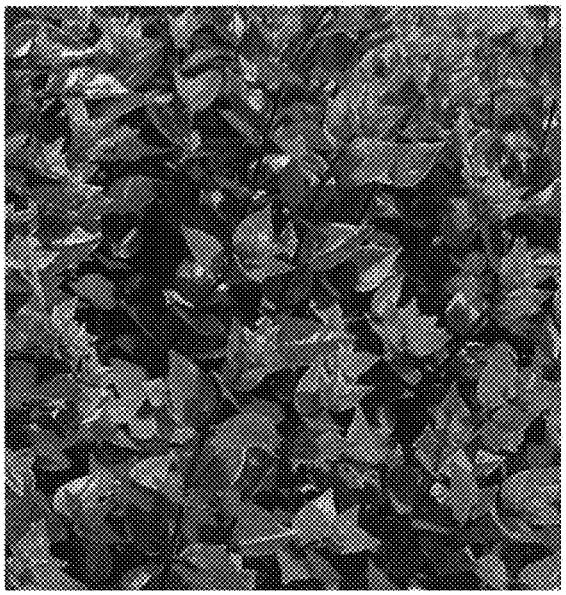

Botanical designation: *Abelia* hybrid.
Cultivar denomination '00-BC-47-7R'.

BACKGROUND OF THE INVENTION

The present invention relates to a new and distinct cultivar of the ornamental flowering shrub *Abelia* hereinafter referred to by the varietal denomination '00-BC-47-7R'.

The new *Abelia* '00-BC-47-7R' is a product of a planned breeding program conducted by the inventors in Griffin, Ga. The objective of the *Abelia* breeding is to produce a tough and adaptable drought-tolerant plant with commercial value. The new '00-BC-47-7R' has significant commercial and home gardener appeal with its glossy foliage, uniform and compact mounding form, relatively short height, white flowers with greyed-orange or yellow-green sepals, heavy blooming, and low maintenance requirements. These and other qualities are enumerated herein.

The new '00-BC-47-7R' originated from a cross in 1999 between an *Abelia* hybrid '99-2-8' (unpatented, female parent) and an *Abelia grandiflora* 'Francis Mason' (unpatented, male parent). The female parent *Abelia* '99-2-8' originated from a cross in 1998 between an unnamed *Abelia chinensis* plant of unknown origin (unpatented, female grandparent) and *Abelia grandiflora* 'Francis Mason' (unpatented, male grandparent).

Seedlings from the cross between the female parent *Abelia* '99-2-8' and the male parent *A. grandiflora* 'Francis Mason' were planted in a field plot in Griffin, Ga. (cold hardiness zone 8a) in the fall of 2003. Plants were evaluated for flowering and foliage characteristics, plant form and height, cold hardiness and drought tolerance. Plant '00-BC-47-7R' was selected and vegetatively propagated by stem cuttings in Griffin, Ga. In the summer of 2008, '00-BC-47-7R' was planted with five other selections into a field plot in Griffin, Ga. in a completely randomized design with four replications per selection. In summer of 2011, '00-BC-47-7R' was planted into a field plot in Blairsville, Ga. (cold hardiness zone 7a), along with 4 other selections. This plot had four replicates per selection in a randomized complete block design.

Asexually propagated '00-BC-47-7R' plants have been evaluated in Griffin for 12 years, and in Blairsville for 9 years. In Griffin, height and widths were measured for the first time in March 2010; following measurements, half of the plants were pruned every two years to a height of 40 to 50 cm and half were left unpruned. Height and width data were collected in Griffin every two years prior to pruning. First bloom dates were recorded each year. Winter cold and spring frost damage were assessed each spring in Griffin and Blairsville. Observation for disease or insect damage was continuous throughout the summer. Asexual reproduction of the new *Abelia* '00-BC-47-7R' by softwood stem cuttings since 2008 has shown that the unique features of this new *Abelia* are stable and reproduced true to type in successive generations.

SUMMARY OF THE INVENTION

The new *Abelia* cultivar '00-BC-47-7R' has not been observed under all possible environmental conditions. The phenotype may vary somewhat with variations in environment and cultural practices such as temperature, water and fertility levels, soil types, and light intensity without, however, any variance in genotype.

*Abelia* is a genus of 15-30 species and interspecific hybrids that are popular landscape plants. They range from deciduous to evergreen, depending upon the cultivar and the climate. They have attractive, colorful foliage and flower from late spring to autumn. *Abelia* is a low-maintenance shrub that is tolerant of any well-drained soil, has heat and drought tolerance and is resistant to most pests. It thrives in full sun or part shade, and can generally be grown in cold hardiness zones 5 through 9. The new plant is expected to be distributed for landscape use in the U.S. and perhaps in other countries.

The following traits have been consistently observed in the original and asexually propagated plants of this new variety in both Blairsville and Griffin, Ga., and to the best knowledge of the inventors, their combination are determined to be the unique and distinguishing characteristics of the new *Abelia* cultivar named '00-BC-47-7R'. In combination, these traits set '00-BC-47-7R' apart from all other existing varieties of *Abelia* known to the inventors:

1. uniform, compact, mounding growth habit and (see, e.g., FIGS. 1A-1C, 3A-3D and 4A-4D);
2. shorter height than its parents and many other cultivars (see Tables 1 and 2);
3. foliage that is glossy (see FIG. 2A), yellow-green to green in spring (FIGS. 1A and 2A, changing to dark green in summer (FIGS. 3A and 5A);
4. wide, compound panicles with many subpanicles per panicle (Table 4); and
5. white flowers with greyed-orange or yellow-green sepals (FIGS. 5A-5D, Table 6).

Comparison: The new variety of *Abelia* '00-BC-47-7R' can be compared to its male parent 'Francis Mason' and maternal grandparent *A. chinensis* and to 'Rose Creek' (unpatented), a cultivar it most closely resembles. The female parent *Abelia* hybrid '99-2-8' was never propagated or sold, and the plant was discarded in 2001. It is known that '99-2-8' had yellow foliage, but further comparison data is not available. The new *Abelia* '00-BC-47-7R' can also be compared to sibling cultivar '00-BC-47-13R' (U.S. Plant application Ser. No. 17/317,299), which is taller in height than '00-BC-47-7R'. Summer foliage of '00-BC-47-7R' is glossier and a darker green than the yellow-green foliage of '00-BC-47-13R' in the summer, and the sepals of '00-BC-47-7R' are greyed-orange or yellow-green compared to those of '00-BC-47-13R', which are orange-red in late summer.

'00-BC-47-7R' plants have been evaluated in field plots in Griffin, Ga. and in Blairsville, Ga. One plant of *A. chinensis* (maternal grandparent) and 'Francis Mason' (paternal parent) have been grown in Griffin since 2001. 'Francis Mason' was asexually propagated, and six replicates were planted in Blairsville in 2003 and six replicates were planted in Griffin in 2009. 'Rose Creek' was used as a standard for comparison as it is a popular cultivar that has *A. chinensis* as a maternal parent. 'Rose Creek' was planted in Griffin with replicates in 2004, 2006 and 2009, and in Blairsville in 2003. Height and width data were collected in Griffin every year. Half of the plants were pruned every two years, while the other plants were not pruned to provide information on mature size. First bloom dates were recorded each year. Winter cold and spring frost damage was assessed each spring in Griffin and Blairsville. Observation for disease or insect damage was continuous throughout the summer.

Foliage of '00-BC-47-7R' is glossy yellow-green to green in June, changing to dark green in the summer. 'Francis Mason' has golden yellow foliage; 'Rose Creek' and *A. chinensis* have green foliage (see all FIGS.).

Height of pruned '00-BC-47-7R' is statistically shorter than 'Francis Mason', *A. chinensis* and 'Rose Creek' (Table 1). Width of '00-BC-47-7R' is similar to 'Rose Creek' and smaller than 'Francis Mason' and *A. chinensis* (Table 1). Height and width of unpruned '00-BC-47-7R' is less than 'Francis Mason' and 'Rose Creek' (Table 2).

Figure 3A:
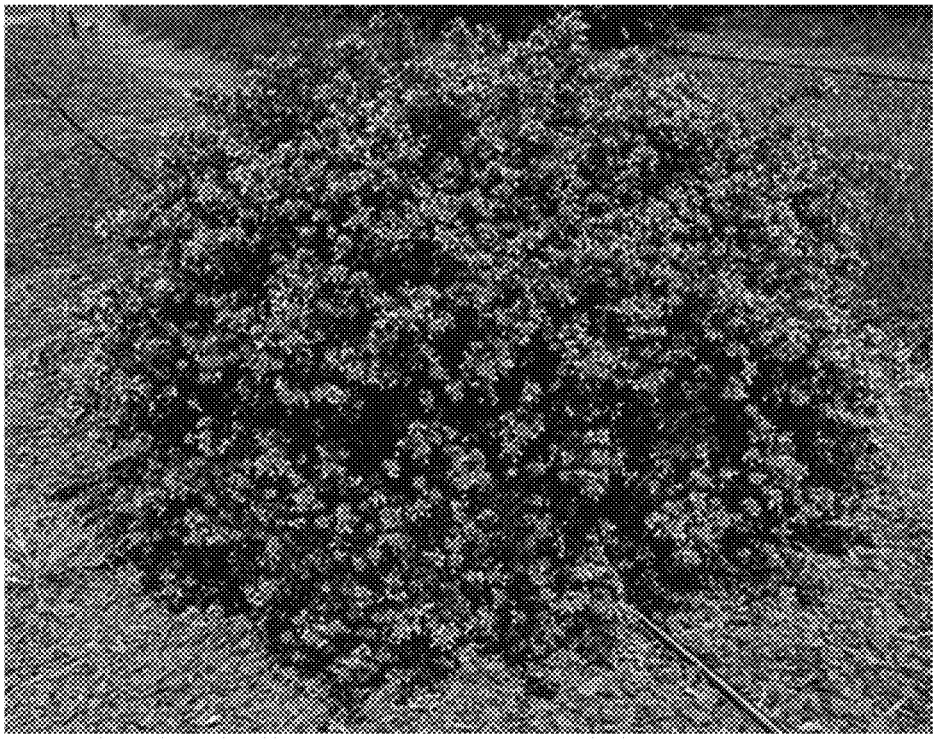
Figure 3B:
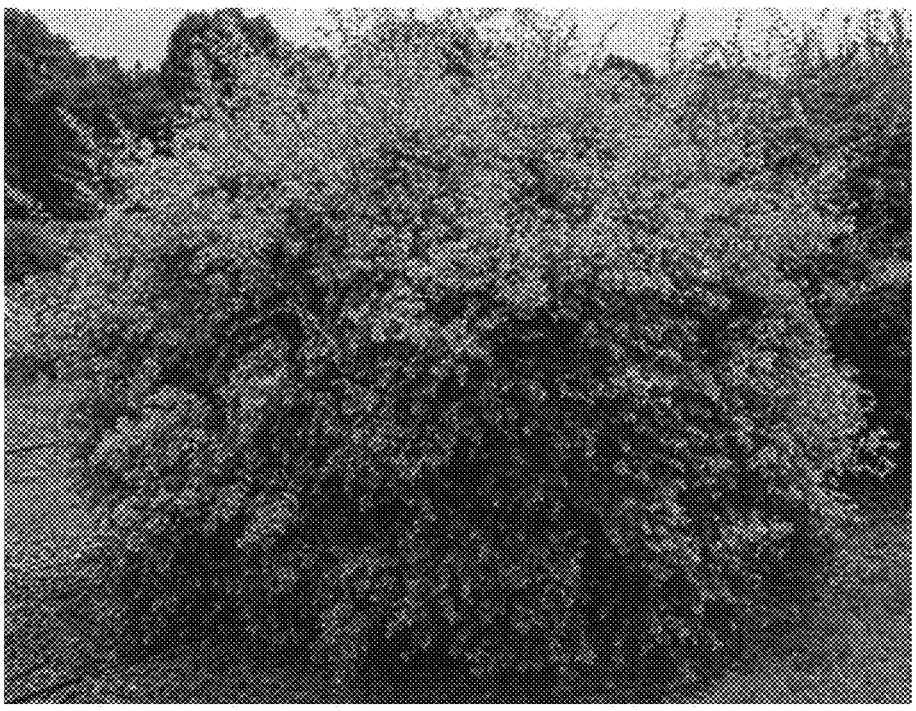
Figure 3C:
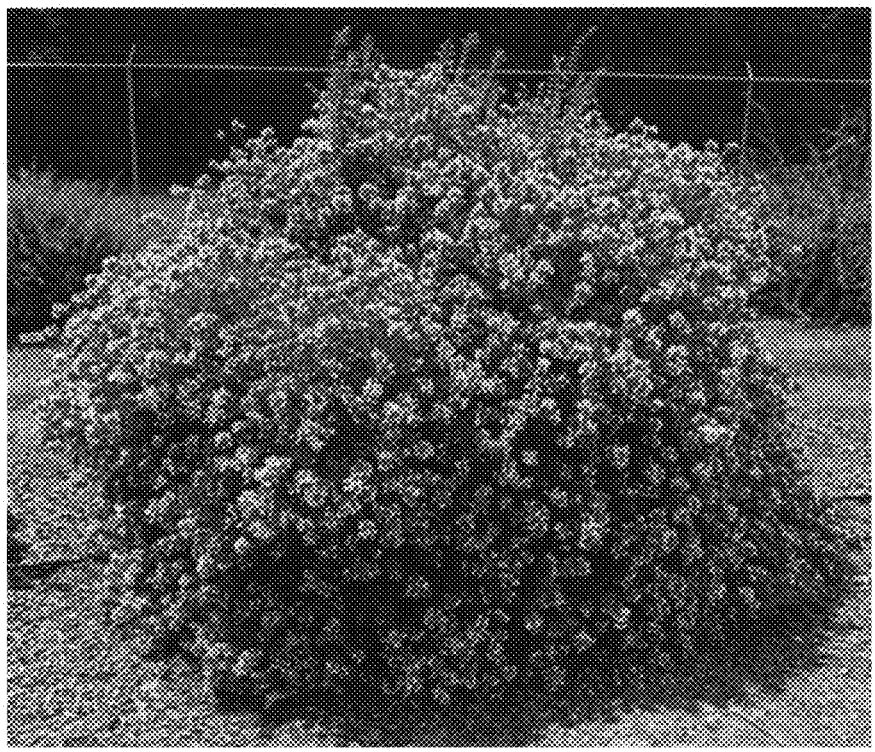
Figure 4A:
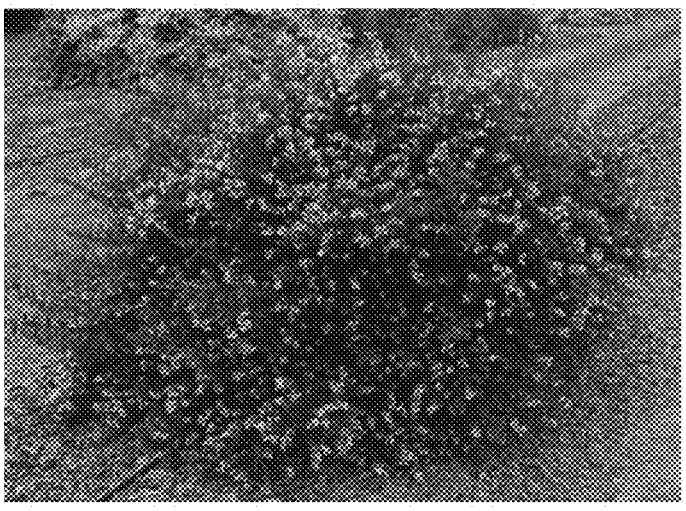
Figure 4B:
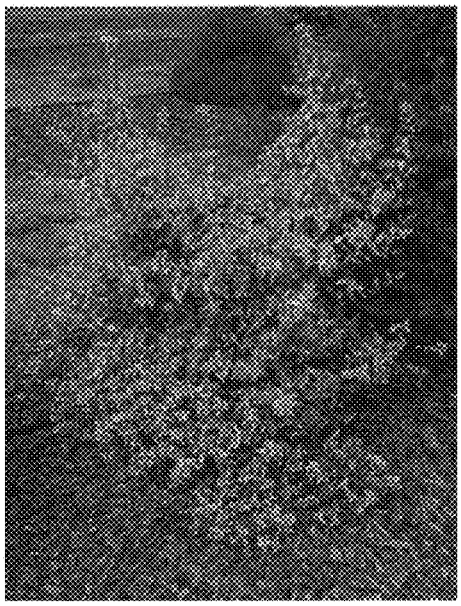
Figure 4C:
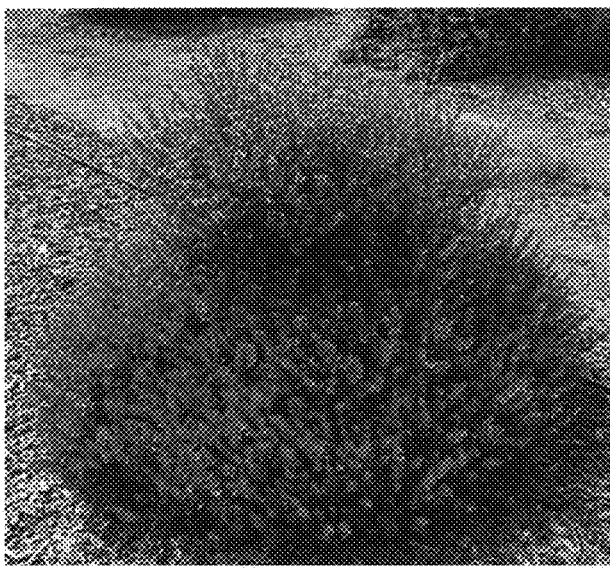

The variety '00-BC-47-7R' begins blooming about one week later than 'Francis Mason' but about two to three weeks earlier than *A. chinensis* and 'Rose Creek' (Table 3). The variety '00-BC-47-7R' blooms from May to September, with heavy blooming in June through August in Griffin (FIGS. 3A and 4A).

The flowers of '00-BC-47-7R' occur in compound panicles, mostly terminal though some are axillary. The panicles of '00-BC-47-7R' average about 37 cm in length and 33 cm width. The length of 'Francis Mason' is significantly greater than that of '00-BC-47-7R', though widths are similar. Both *A. chinensis* and 'Rose Creek' are shorter and narrower than '00-BC-47-7R' (Table 4, FIGS. 5A-5D). The number of subpanicles per compound panicle averages about 74 on '00-BC-47-7R', statistically similar to the 56 on 'Francis Mason'; *A. chinensis* and 'Rose Creek' have fewer subpanicles than '00-BC-47-7R' (Table 4).

Figure 5A:
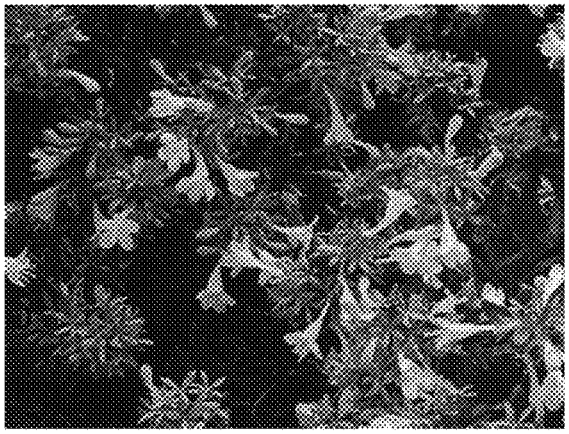
Figure 5B:
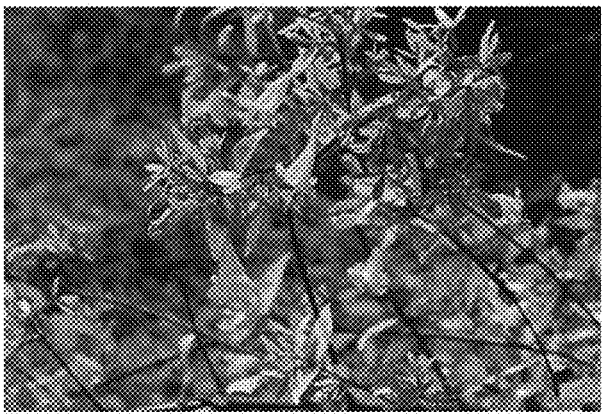
Figure 5C:
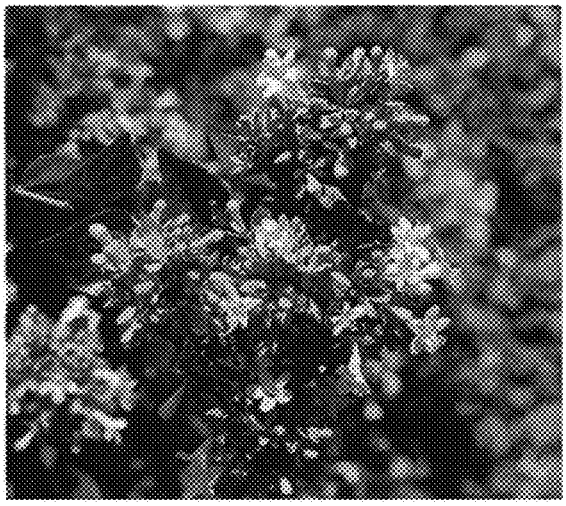

Flowers of '00-BC-47-7R', 'Francis Mason', *A. chinensis*, and 'Rose Creek' are white (FIGS. 5A-5D, Table 5); sepals of '00-BC-47-7R' are greyed-orange and yellow-green (FIG. 5A, Table 6); 'Francis Mason' is greyed-red in mid-summer and orange-red in late summer (FIG. 5B, Table 6); *A chinensis* is greyed-red and yellow-green in mid-summer and greyed-orange and yellow-green in late summer (FIG. 5D, Table 6), and 'Rose creek' is red-purple in mid-summer changing to red in late summer (FIG. 5C, Table 6). Flowers of '00-BC-47-7R' are similar in length to 'Francis Mason' and longer than *A. chinensis* and 'Rose Creek'. Flower width of '00-BC-47-7R' is narrower than 'Francis Mason' and 'Rose Creek', but similar to *A. chinensis* (Table 5).

Plants of '00-BC-47-7R' in the Griffin field plot had no frost or cold damage in 2014, a winter that was very cold, with a low of 5.6° F. in January. Minor damage was observed on five plants in 2015. This was likely due to a late spring freeze of 26° F. on March 29. No damage occurred in 2018, and one plant suffered minor damage in 2019 (Table 7). Both 'Francis Mason' and 'Rose Creek' had plants with minor, moderate or major cold damage in 2015. 'Rose Creek' also had two plants with minor damage in 2019. The single plant of *A. chinensis* showed no damage in any of these years (Table 7). All four plants of '00-BC-47-7R' planted in Blairsville Ga. (Zone 7a) in 2011 have survived. One plant had moderate cold damage from the winter of 2012 but recovered completely by summer. Damage was also observed in spring 2014, where all four plants had cold damage, but all completely recovered. The winter of 2014 was the coldest in Blairsville since 2011, with a −4.6° F. recorded in January.

As established, three checks were used for comparison to '00-BC-47-7R' (parents 'Francis Mason' and *A. chinensis*, and 'Rose Creek'), and all are distinctly different. Plant '00-BC-47-7R' is shorter than the check cultivars (Tables 1 and 2). 'Francis Mason' blooms about a week earlier in May than does '00-BC-47-7R', while *A. chinensis* and 'Rose Creek' are later (Table 3). Panicle length of '00-BC-47-7R' is shorter than 'Francis Mason', but longer than the other check cultivars. Width of the compound panicle and number of subpanicles per panicle is similar for both '00-BC-47-7R' and 'Francis Mason', and greater than *A. chinensis* and 'Rose Creek' (Table 4). All have white flowers (FIGS. 5A-5D, Table 5). *A. chinensis* has sepal color similar to '00-BC-47-7R' (Table 6).

The new *Abelia* '00-BC-47-7R' is readily propagated through cuttings. Six-inch cuttings taken in May or early June before flowering rooted at a rate of over 70%. After 2 months, cuttings can be transferred to one-gallon containers using a well-drained potting mix. From cutting to saleable plant is about 8 months. No insect or disease problems have been noted in potted plants maintained outside the greenhouse, or in field plants. Once established, the plants are quite drought resistant. After landscape establishment, a hard pruning is recommended in early spring approximately every other year to encourage compact growth and heavy blooming The new variety '00-BC-47-7R' has a uniform, mounding growth habit. White flowers and greyed-orange or yellow-green sepals are borne on large compound panicles. Blooming is very heavy from May to September. Blooming is heavy even on young plants in containers or in the field.

TABLE 1

Height and width (cm) of '00-BC-47-7R', 'Francis Mason', 'Rose Creek' and *A. chinensis* in a field plot in Griffin, GA in November 2019. Plants were pruned every two years to a height of about 40 to 50 cm, depending upon the maturity of the plant. Data are from plants that had been pruned in November 2017 and had been in the field at least 9 years. One plant of '00-BC-47-7R' was planted into the field in 2003. One plant of each parent and 'Rose Creek' was planted in 2001. Reps of '00-BC-47-7R' were planted in the field in 2008, 'Francis Mason' in 2009 and 2011, and 'Rose Creek' in 2004, 2006 and 2009.

| Genotype | Rep # | Height (cm) | Width (cm) |
|---|---|---|---|
| '00-BC-47-7R' | 3 | 116 ± 4.4* | 203.2 ± 7.1 |
| 'Francis Mason' | 3 | 167 ± 5.1 | 240 ± 5.3 |
| *A. chinensis* | 1 | 256 | 308 |
| 'Rose Creek' | 6 | 140.3 ± 5.0 | 206.1 ± 6.5 |

*Standard error of the means at the 95% confidence level.

TABLE 2

Height and width (cm) of unpruned plants of '00-BC-47-7R', 'Francis Mason' and 'Rose Creek' in a field plot in Griffin, GA in 2019. Data are from plants that were in the field at least 9 years. Reps of '00-BC-47-7R' were planted in the field in 2008, 'Francis Mason' in 2009 and 2011, and 'Rose Creek' in 2004, 2006 and 2009.

| Genotype | Rep # | Height (cm) | Width (cm) |
|---|---|---|---|
| '00-BC-47-7R' | 2 | 150 ± 24* | 239.2 ± 14.8 |
| 'Francis Mason' | 4 | 210.2 ± 10.9 | 280.4 ± 11.4 |
| 'Rose Creek' | 4 | 203 ± 9.7 | 346.9 ± 16.2 |

*Standard error of the means at the 95% confidence level.

TABLE 3

Week of first bloom for '00-BC-47-7R', 'Francis Mason', *A. chinensis* and 'Rose Creek' in a Griffin field plot in 2011, 2015, 2017 and 2019. The number in parentheses is the number of plants that bloomed on that date.

| Genotype | 2011 | 2015 |
|---|---|---|
| '00-BC-47-7R' | 5-9 (1); 5-16 (5) | 5-25 (1); 6-1 (2); 6-8 (2) |
| 'Francis Mason' | 5-9 (4) | 5-18 (6) |
| *A. chinensis* | 6-6 (1) | 6-15 (1) |
| 'Rose Creek' | 5-30 (1); 6-6 (9); 6-13 (2) | 6-8 (1); 6-15 (3); 6-22 (2); 6-29 (1) |
| **Genotype** | **2017** | **2019** |
| '00-BC-47-7R' | 5-15 (5) | 5-20 (3); 5-27 (2) |
| 'Francis Mason' | 5-1 (1); 5-8 (4); 5-15 (1) | 5-13 (4); 5-20 (2) |
| *A. chinensis* | 6-5 (1) | 6-17 (1) |
| 'Rose Creek' | 5-22 (2); 5-29 (7); 6-5 (2) | 6-3 (11); 6-10 (1) |

TABLE 4

Comparison of morphological traits of compound panicles of '00-BC-47-7R', 'Francis Mason', *A. chinensis* and 'Rose Creek'. Data were collected from field-grown plants in full sun in Griffin, Georgia on Jun. 16 or Jul. 30, 2020, depending upon time of full bloom.

| Cultivar | Compound panicle length[1] (mm) | Compound panicle width[1] (mm) | Number of subpanicles per compound panicle |
|---|---|---|---|
| '00-BC-47-7R' | 367.0 b[2] | 330.5 a | 73.5 a |
| 'Francis Mason' | 457.6 a | 389.5 a | 55.5 a |
| *A. chinensis* | 181.6 c | 163.6 b | 20.3 b |
| 'Rose Creek' | 104.6 d | 128.5 c | 6.3 c |

[1]Length and width of compound panicles and number of subpanicles were measured on the ten longest compound panicles on a plant of similar age.
[2]Means of lengths and widths were compared across genotypes using t-tests. Means followed by different letters are significantly different $P < 0.05$.

TABLE 5

Flower color and size of '00-BC-47-7R', 'Francis Mason', *A. chinensis* and 'Rose Creek'.

| Cultivar | Petal-upper surface | Petal-lower surface | Flower length[1] (mm) | Flower Width[1] (mm) |
|---|---|---|---|---|
| '00-BC-47-7R' | White NN155C | White NN155C Red-Purple 62D | 15.1a | 8.4a |
| 'Francis Mason' | White N155B | White N155B | 16.3a | 11.9b |
| *A. chinensis* | White NN155D | White N155B | 13.1b | 8.9a |
| 'Rose Creek' | White N155C | White N155C | 12.2b | 11.9b |

[1]Means of flower lengths and widths were compared across genotypes using t-tests. Means followed by different letters are significantly different $P < 0.05$.

TABLE 6

Sepal color of '00-BC-47-7R', 'Francis Mason', *A. chinensis* and 'Rose Creek'

| Cultivar | Mid-summer | Late-summer |
|---|---|---|
| '00-BC-47-7R' | Greyed-Orange 175A with 144C Yellow-Green base | Greyed-Orange 173A; Yellow-Green 145A |

TABLE 6-continued

Sepal color of '00-BC-47-7R', 'Francis Mason', *A. chinensis* and 'Rose Creek'

| Cultivar | Mid-summer | Late-summer |
|---|---|---|
| 'Francis Mason' | Greyed-Red 179C | Orange-Red 35C |
| *A. chinensis* | Greyed-Red 179C; Yellow-Green 144B | Greyed-Orange 174C; Yellow-Green 145A |
| 'Rose Creek' | Red-Purple 59D | Red 51C |

TABLE 7

Number of plants of '00-BC-47-7R' and check cultivars with cold or frost damage in the Griffin field plot in 2014, 2015, 2018 and 2019. Plants were classified as having no damage, or minor, moderate or severe damage.

| Cold/frost damage | Year | '00-BC-47-7R' | 'Francis Mason' | 'Rose Creek' | *A. chinensis* |
|---|---|---|---|---|---|
| None | 2014 | 5 | 7 | 10 | 1 |
| | 2015 | 0 | 0 | 0 | 1 |
| | 2018 | 5 | 8 | 12 | 1 |
| | 2019 | 4 | 8 | 10 | 1 |
| Minor | 2014 | 0 | 0 | 0 | 0 |
| | 2015 | 5 | 4 | 3 | 0 |
| | 2018 | 0 | 0 | 0 | 0 |
| | 2019 | 1 | 0 | 2 | 0 |
| Moderate | 2014 | 0 | 0 | 0 | 0 |
| | 2015 | 0 | 2 | 6 | 0 |
| | 2018 | 0 | 0 | 0 | 0 |
| | 2019 | 0 | 0 | 0 | 0 |
| Severe | 2014 | 0 | 0 | 0 | 0 |
| | 2015 | 0 | 1 | 3 | 0 |
| | 2018 | 0 | 0 | 0 | 0 |
| | 2019 | 0 | 0 | 0 | 0 |

Notes: Winter of 2014 was very cold, especially January. The minimum temperature of 5.6° F. occurred on January 7, and temperatures below 20° F. were recorded eight times that month. November of 2013 was also exceptionally cold, with a low of 15.8° F. on November 19. Winter of 2015 had a minimum temperature of 9.6° F. in January as well as several days of 15° F. in January and February. A late spring freeze of 26.2° F. occurred on March 29. Winter of 2018 was cold in January, with temperatures ranging from 10.9° F. to 17.5° F. on six days that month. February was warm, though 25.8° F. occurred on March 9. Fall was mild. Winter of 2019 was warm. The minimum temperature was 20.8° F. on January 30. Fall was mild.

BRIEF DESCRIPTION OF THE PHOTOGRAPHS

The accompanying colored photographic illustrations show the overall appearance and distinct characteristics of the new cultivar of *Abelia* '00-BC-47-7R' showing the colors as true as possible. Colors in the photographs may differ slightly from the color values cited in the detailed botanical description, which accurately describes the colors of the new *Abelia* '00-BC-47-7R'. The photographs were taken of plants grown outdoors in Griffin and Blairsville, Ga. on various dates as noted below.

The photographs labeled FIGS. 1A-1C depict the overall plant habit and foliage color in late spring/early summer of '00-BC-47-7R' (FIG. 1A) as compared to 'Francis Mason' (FIG. 1B) and 'Rose Creek' (FIG. 1C), all taken on Jun. 3, 2020 in Griffin, Ga.

Figure 2D:
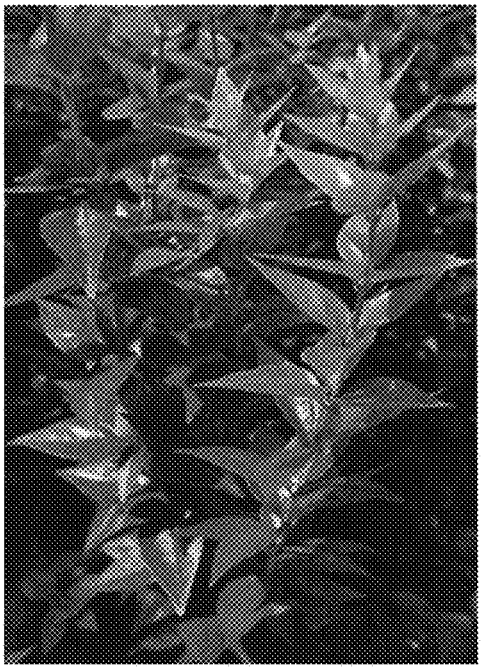

The photographs labeled FIGS. 2A-2D depict close-up views of the early summer foliage of '00-BC-47-7R' (FIG. 2A, taken Jun. 3, 2020) as compared to 'Francis Mason' (FIG. 2B, taken Jun. 18, 2020), 'Rose Creek' (FIG. 2C, taken Jun. 3, 2020), and *A. chinensis* (FIG. 2D, taken Jun. 18, 2020).

Figure 3D:
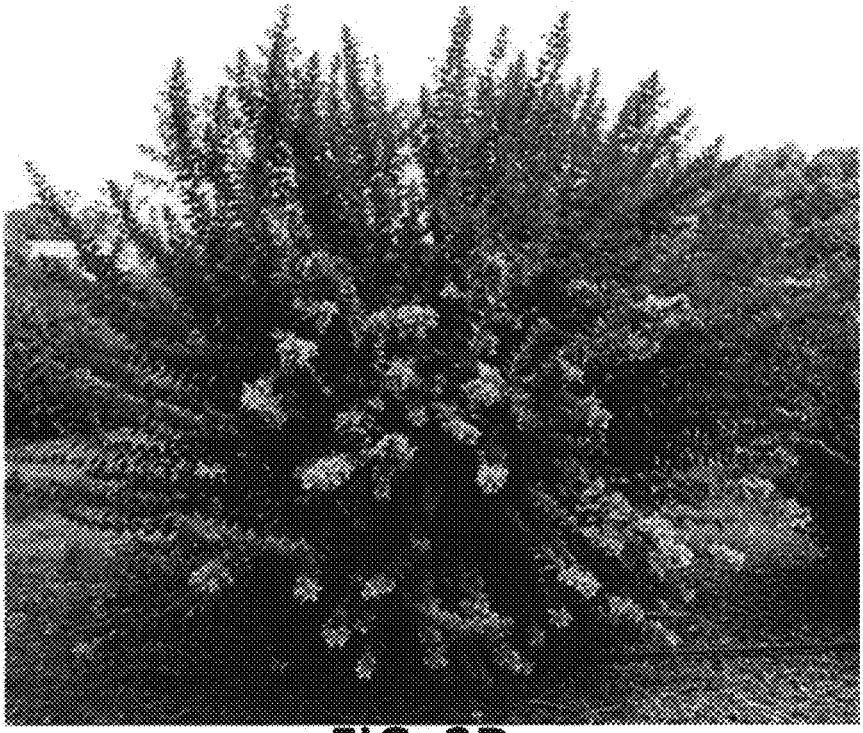

The photographs labeled FIG. 3A-3D depict full bloom of '00-BC-47-7R' (FIG. 3A, taken Jul. 23, 2020), 'Francis Mason' (FIG. 3B, taken Jun. 18, 2020), 'Rose Creek' (FIG. 3C, taken Aug. 5, 2018), and '*A. chinensis*' (FIG. 3D, taken Jul. 23, 2020).

Figure 4D:
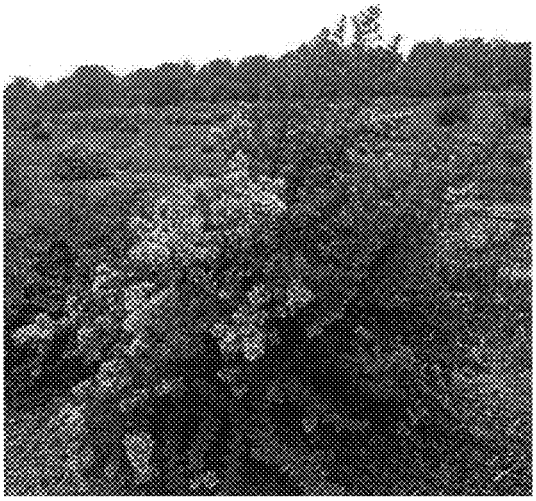

The photographs labeled FIGS. 4A-4D depict growth habit of '00-BC-47-7R' (FIG. 4A, taken Jun. 5, 2019) compared to 'Francis Mason' (FIG. 4B, taken Jun. 4, 2019), 'Rose Creek' (FIG. 4C, taken Jun. 4, 2019), and *A. chinensis* (FIG. 4D, taken Jul. 23, 2008).

Figure 5D:
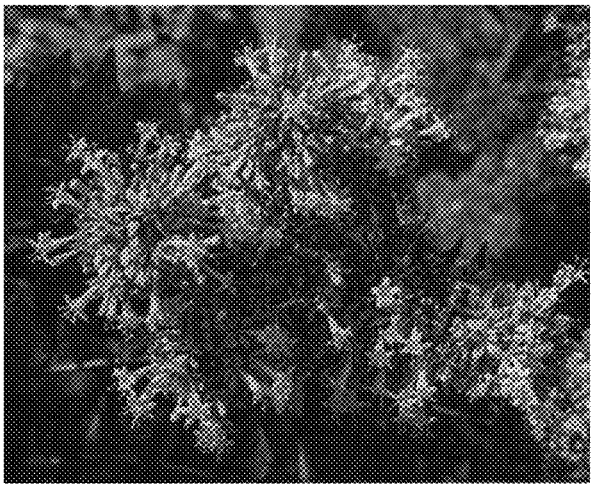

The photographs labeled FIG. 5A depict close-up views of the flowers and sepals of '00-BC-47-7R' (FIG. 5A, taken Aug. 27, 2020), compared to 'Francis Mason' (FIG. 5B, taken Jun. 18, 2020), 'Rose Creek' (FIG. 5C, taken Aug. 8, 2019) and *A. chinensis* (FIG. 5D, taken Aug. 8, 2019).

DETAILED BOTANICAL DESCRIPTION

The following traits have been consistently observed in the original plant of this new variety and in asexually propagated progeny grown from stem cuttings in Griffin and Blairsville, Ga., and, to the best knowledge of the inventors, their combination forms the unique characteristics of the new variety '00-BC-47-7R'.

Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society, London, England in 2007, except where general terms of ordinary dictionary significance are used.

The aforementioned photographs and following observations, measurements, and values describe plants of the *Abelia* cultivar named '00-BC-47-7R'. Where dimensions, sizes, colors, and other characteristics are given, it is to be understood that such characteristics are approximations and averages set forth as accurately as practicable.

Data were collected from '00-BC-47-7R' plants propagated from softwood stem cuttings and grown in one-gallon containers prior to planting in field plots in Griffin, Ga. Data are from plants planted and grown in the field since 2003 and 2008. The average low temperature for the year ranges from about 38° F. in January to 72° F. in July, and the average high temperature for the year ranges from about 54° F. in January to 88° F. in July for Griffin. In Blairsville, the average low temperature ranges from about 29° F. in January to 62° F. in July and the average high ranges from 45° F. in January to 84° F. in July.

Botanical classification: *Abelia* '00-BC-47-7R'.

*Commercial classification.*—Shrub.

*Parentage.*—Cross between an *Abelia* hybrid plant labeled '99-2-8' (unpatented female parent, which originated from a cross between an unnamed *Abelia chinensis* plant and unpatented plant *A. grandiflora* named 'Francis Mason') and an *Abelia grandiflora* 'Francis Mason' (unpatented male parent).

Growth and propagation:

*Propagation type*.—By softwood stem cuttings.

*Growth rate*.—Softwood cuttings rooted in 3 weeks at an approximate temperature of about 80° F. under the mist.

*Root description*.—White, dense, freely branched.

*Rooting habit*.—Fibrous.

Plant description:

*Form*.—Partially deciduous shrub that retains about 50 to 80% of its leaves, with heavy blooming of white flowers and greyed-orange and yellow-green sepals.

*Habit*.—Uniform, compact, mounding.

*Usage*.—Various uses, such as container patio plants, potted plants, landscape uses such as border, hedge, and mass planting.

*Vigor*.—Moderately vigorous.

*Size of plant*.—A. Height: about 1.5 m on unpruned plants in field for 11 years. B. Width: about 2.4 m on unpruned plants in field for 11 years.

*Stem*.—Mostly upright, some mature branches arching. A. First year. 1. Color (R.H.S.): Greyed-Orange 173A. 2. Diameter: about 2 mm; length: about 64 cm. 3. Pubescence: covered in minute curved hairs. 4. Exfoliation/Texture: smooth. 5. Shape: Round. 6. Pith. a. Type: solid. b. Diameter: (measured halfway from apex to start of one year's growth) about 2.0 mm. c. Color (R.H.S.): Yellow-Green 153A. 7. Odor (of bruised stem): Cut grass (faint). 8. Lenticels. a. Number: none observed. 9. Internode length (average of about 5-10 internodes in middle of first year shoots) about 15 mm. 10. Strength: very strong. B. Second Year. 1. Color (R.H.S.): Greyed-Orange 177A with Greyed-yellow 161B striations. 2. Diameter: about 4.0 mm. 3. Exfoliation/Texture: Mostly smooth, developing lengthwise cracks along stem.

*Vegetative buds*.—A. Arrangement: opposite or ternary. B. Type: valvate. C. Size (length×width): about 0.5 mm×0.5 mm. D. Scale Number: about 2, sometimes 3. E. Scale Color (R.H.S.): Greyed-Purple 183A. F. Position/Disposition (angle to stem): about 45°. G. Number at Node: about 2 vegetative single, about 3 if ternary. H. Pubescence: scattered, very short hairs. I. Shape: lanceolate.

*Leaf scar*.—A. Shape: rounded crescent. B. Vascular Bundle Traces (number, orientation): three horizontal across scar. C. Pubescence: sparse, short hairs around scar margin. D. Position of Bud (on leaf scar): about 45° in axis. E. Color Differentiation (R.H.S.): Greyed-Yellow 161B. F. Size (h×w): about 1 mm×1 mm.

*Trunk or large stems*: A. Color(s) (R.H.S.): Greyed-Orange 177A with Greyed-Yellow 161B striations. B. What Size Stem Exfoliation beings on: about 3 mm. C. Diameter: about 10-15 mm. D. Texture: longitudinal cracks.

*Leaf*.—A. Leaf type: simple, entire. B. Color Through Season (always R.H.S.). 1. Emerging: April. Upper: Yellow-Green 147B with Greyed-Orange 176B on leaf margin; Lower: Yellow-Green 144B. 2. Summer: August. Upper: Green N137B; Lower: Yellow-Green 147C. 3. Fall: November. Upper: Greyed-Green N189A, very glossy; Lower: Yellow-Green 146B. 4. Winter: December. Upper: Very glossy Yellow-Green 147A or Brown 200A; Lower: Yellow-Green 146B or yellow-Green 147B. C. Mature size (L×W): about 1.5 cm×about 2.5 cm; thickness: 0.26 mm. D. Apex: acute. E. Base: rounded, equilateral. F. Margin: slightly crenate. G. Shape: lanceolate. H. Lobes (present/absent): absent. I. Vein color (R.H.S.): Yellow-Green 147D. J. Pubescence: 1. Upper Surface: sparse tiny hairs. 2. Lower surface: hairs concentrated along lower one-half of the midvein; single row of hairs around leaf margin. K. Arrangement on stem: mostly opposite, some trifoliate. L. Venation: simple alternate. M. Texture: Degree of waxiness of surface: slightly waxy. N. Odor when crushed: faint grassy.

*Petiole*.—A. Length: about 2-4 mm. B. Shape: slightly curved and concave. C. Color (R.H.S.): Green 137A. D. Pubescence: sparse along edges, scattered short, curved hairs on reverse side. E. Diameter: about 0.7 mm.

*Inflorescence(s)*.—A. Type: Compound panicle, terminal and axillary. B. Number per Plant: about 500 to 1000, depending upon size of mature plant. C. Size (L×W): single inflorescence about 3.5-5 cm×5-5 cm; compound panicle, about 37 cm×33 cm; about 74 subpanicles per compound panicle. D. Color (R.H.S.): 1. At emergence: White 155D. 2. Full bloom: White NN155C. 3. Fading: White 155B. E. Longevity: June to frost. F. Peduncle. 1. Length: about 1 cm. 2. Diameter: about 1 mm. 3. Color (R.H.S.): Greyed-Orange 165A. 4. Pubescence: covered in very short glandular hairs. 5. Strength: strong. 6. Aspect: about 45° to stem.

*Flower*.—A. Number per Inflorescence: about 20-50 in various stages of bloom. B. Axillary or Terminal: axillary. C. Symmetry: regular, actinomorphic. D. Size (l×w): about 15 mm×8 mm; Depth: about 9 mm. E. Pubescence: outside, short glandular hairs; inside, short glandular hairs with longer hairs extending into calyx throat. F. Texture: punticulate. G. Color at peak bloom (R.H.S.): 1. Upper surface: White NN155C. 2. Lower surface: White NN155C. H. Fragrance: mildly sweet. I. Time of full maturity: spring. J. Time range for showiness: early May until frost. K. Bud: 1. Size (l×w): about 10 mm×3 mm. 2. Shape: elongated teardrop, curved. 3. Color (R.H.S.): White N155C. 4. Pubescence: covered in tiny glandular hairs. 5. Longevity: 1 week. L. Petals: 1. Number: one. 2. Size (l×w): about 15 mm×8 mm. 3. Shape: funnel, slightly tubular, gamopetalous. 4. Apex: usually 5 lobes, rounded and slightly curled. 5. Base: funnel shaped with short tube about ⅓ the length of the flower. 6. Margin: entire but slightly curled. 7. Color at peak bloom (R.H.S.): upper surface: White NN155C; lower surface: White NN155C with a very slight blush of Red-Purple 62D. 8. Texture: punticulate. 9. Arrangement: N/A. M. Pedicels: 1. Color (R.H.S.): Greyed-Orange 164A. 2. Pubescence: covered in short glandular hairs. 3. Length: about 2-3 mm. 4. Aspect: about 45°. 5. Strength: medium. 6. Diameter: about 1 mm. N. Sepal(s): 1. Number: five. 2. Size (l×w): about 5 mm×2 mm. 3. Shape: elliptic. 4. Apex: rounded. 5. Base: attenuate. 6. Margin: entire, smooth. 7. Texture: slightly punticulate. 8. Pubescence: covered in very short hairs, single row around margin. 9. Color at peak of bloom (R.H.S.): a. Upper surface: Grayed-Orange 175A with Yellow-Green 144C towards the base. b. Lower surfaces:

Greyed-Orange 175A with Yellow-Green 144C towards base or solid Yellow-Green 144C O. Male reproductive structures: 1. Number: 4. 2. Anther: a. Size (l×w): about 1.5 mm×0.5 mm. b. Shape: dorsifixed, linear. c. Color (R.H.S.): Greyed-Green 197B. d. Texture/pubescence: slightly punticulate. 3. Filament: a. Size (l×w): about 16 mm×0.2 mm. b. Color (R.H.S.): White 155D. c. Texture: smooth with short hairs more numerous towards base. 4. Pollen: a. Quantity: sparse. b. Pollen color (R.H.S.): White N155B. P. Female Reproductive structures: 1. Pistil: a. Shape: monostylus free. b. Size (l×w): about 15 mm×0.5 mm. c. Position: epigynous, ovary inferior. d. Color (R.H.S.): White 155D. e. Pubescence: scattered short hairs, more numerous towards base. 2. Stigma: a. Shape: circular, domed. b. Color (R.H.S.): Orange-White 159D. c. Pubescence: punticulate surface has short, clear papillose structures. 3. Style: a. Length: about 15 mm. b. Shape: tubular. c. Color (R.H.S.): White 155D. d. Pubescence: scattered hairs, more numerous toward base. 4. Ovary: a. Shape: oval. b. Number: 1. c. Pubescence: none.

*Fruit*.—A. Type: achene. B. Size (l×w): about 5-6 mm×1.5 mm. C. Color(s) during ripening (R.H.S.): all stages present during bloom season. 1. Early: Green 143C. 2. Mid: Green 143A. 3. Late: Greyed-Brown N199A. D. Shape: grooved cylindrical capsule. E. Number per infructescence: 1. F. Pubescence: covered in short, curved hairs. G. Number of carpels: 1. H. Persistence (effective period): summer to frost.

Disease/pest resistance: No notable diseases or other pest problems have been observed for the new *Abelia* '00-BC-47-7R' that are not also common for other varieties. Plants of the new *Abelia* '00-BC-47-7R' have been observed to have similar resistance to diseases and pests as standard for the genus.

It is claimed:

1. A new and distinct cultivar of *Abelia* plant named '00-BC-47-7R' as illustrated and described herein.

* * * * *

FIG. 1A
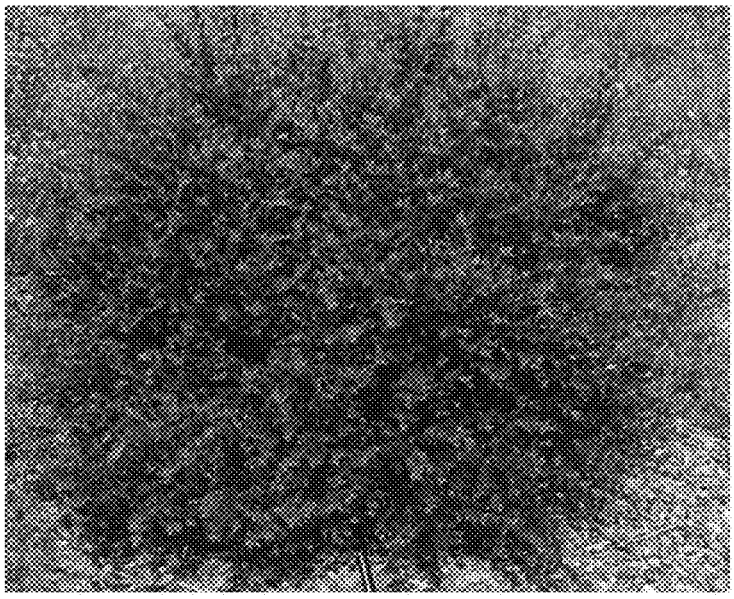
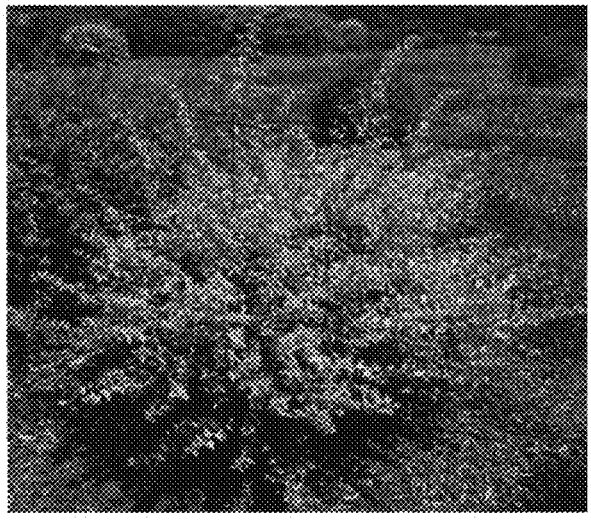
FIG. 1B
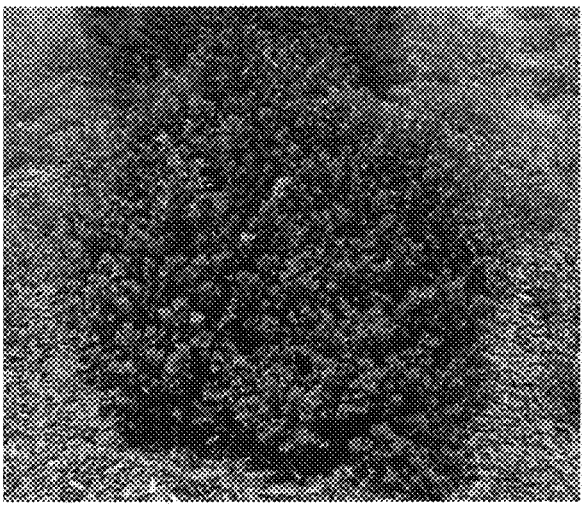
FIG. 1C